US009511087B2

(12) United States Patent
Frieling et al.

(10) Patent No.: US 9,511,087 B2
(45) Date of Patent: Dec. 6, 2016

(54) USE OF ANTITHROMBIN IN EXTRACORPOREAL MEMBRANE OXYGENATION

(71) Applicant: rEVO Biologics, Inc., Framingham, MA (US)

(72) Inventors: Johan Frieling, Natick, MA (US); Simon Lowry, Hillsdale, NY (US)

(73) Assignee: rEVO Biologics, Inc., Framingham, MA (US)

( * ) Notice: Subject to any disclaimer, the term of this patent is extended or adjusted under 35 U.S.C. 154(b) by 0 days.

(21) Appl. No.: 14/239,943

(22) PCT Filed: Aug. 2, 2013

(86) PCT No.: PCT/US2013/053365
§ 371 (c)(1),
(2) Date: Feb. 20, 2014

(87) PCT Pub. No.: WO2014/022748
PCT Pub. Date: Feb. 6, 2014

(65) Prior Publication Data
US 2014/0194360 A1    Jul. 10, 2014

Related U.S. Application Data

(60) Provisional application No. 61/679,345, filed on Aug. 3, 2012.

(51) Int. Cl.
A61K 31/727     (2006.01)
A61K 38/57      (2006.01)

(52) U.S. Cl.
CPC ............ A61K 31/727 (2013.01); A61K 38/57 (2013.01)

(58) Field of Classification Search
CPC .................................................. A61K 31/727
See application file for complete search history.

(56) References Cited

U.S. PATENT DOCUMENTS

| 4,517,294 | A | 5/1985 | Bock et al. |
| 4,632,981 | A | 12/1986 | Bock et al. |
| 4,873,316 | A | 10/1989 | Meade et al. |
| 5,366,894 | A | 11/1994 | Clark et al. |
| 5,576,040 | A | 11/1996 | Moller et al. |
| 5,685,847 | A | 11/1997 | Barry |
| 5,801,063 | A | 9/1998 | Grandics et al. |
| 5,827,690 | A | 10/1998 | Meade et al. |
| 5,843,705 | A | 12/1998 | DiTullio et al. |
| 5,849,992 | A | 12/1998 | Meade et al. |
| 6,268,487 | B1 | 7/2001 | Kutzko et al. |
| 6,441,145 | B1 | 8/2002 | DiTullio et al. |
| 6,528,699 | B1 | 3/2003 | Meade et al. |
| 6,727,405 | B1 | 4/2004 | Gordon et al. |
| 7,019,193 | B2 * | 3/2006 | Ditullio et al. ............ 800/7 |
| 7,045,676 | B1 | 5/2006 | Gordon et al. |
| 7,531,632 | B2 | 5/2009 | Perreault |
| 7,550,263 | B2 | 6/2009 | Meade et al. |
| 7,928,064 | B2 | 4/2011 | DiTullio et al. |
| 7,939,317 | B1 | 5/2011 | Gordon et al. |
| 8,173,860 | B2 | 5/2012 | Meade et al. |
| 8,257,724 | B2 | 9/2012 | Cromack et al. |
| 8,524,688 | B2 | 9/2013 | Ekman-Ordeberg et al. |
| 8,551,096 | B2 | 10/2013 | Perry et al. |
| 2003/0134796 | A1 | 7/2003 | Roemisch et al. |
| 2004/0197930 | A1 | 10/2004 | Rosenfeld et al. |
| 2005/0271660 | A1 | 12/2005 | Wang |
| 2006/0264357 | A1 | 11/2006 | Zikria et al. |
| 2006/0292213 | A1 | 12/2006 | Gerber et al. |
| 2007/0037192 | A1 | 2/2007 | Ziomek et al. |
| 2007/0292407 | A1 | 12/2007 | Ivanov |
| 2008/0026371 | A1 | 1/2008 | Russell et al. |
| 2008/0118501 | A1 | 5/2008 | Schindler et al. |
| 2008/0299594 | A1 | 12/2008 | Rosenfeld et al. |
| 2009/0148458 | A1 | 6/2009 | Russell et al. |
| 2010/0016173 | A1 | 1/2010 | Nagalla et al. |
| 2011/0082083 | A1 | 4/2011 | Magneson et al. |
| 2014/0046033 | A1 | 2/2014 | Schindler et al. |
| 2014/0194360 | A1 | 7/2014 | Frieling et al. |
| 2014/0206617 | A1 | 7/2014 | Frieling et al. |
| 2014/0242182 | A1 | 8/2014 | Evans et al. |
| 2016/0129115 | A1 | 5/2016 | Magneson et al. |

FOREIGN PATENT DOCUMENTS

EP        0 475 354        3/1992

OTHER PUBLICATIONS

Soff, Mar. 2012, A New Generation of Oral Direct Anticoagulants, Arterioscler Thromb Vasc Biol, 32: 569-574.*
Niebler et al., 2011, Antithrombin Replacement During Extracorporeal Membrane Oxygenation, Artificial organs, 35(11): 1024-1028.*
Agati et al., 2006, Use of a Novel Anticoagulation Strategy During ECMO in a Pediatric Population: Single-Center Experience, ASAIO Journal, 52: 513-516.*
Agati et al., Use of a novel anticoagulation strategy during ECMO in a pediatric population: single-center experience. ASAIO J. Sep.-Oct. 2006;52(5):513-6.
Buck, Antithrombin Administration during Pediatric Extracorporeal Membrane Oxygenation. Pediatric Pharmacotherapy: A Monthly Newsletter for Health Care Professionals from the University of Virginia Children's Hospital. Feb. 2013; 19(2): 4 pages.

(Continued)

Primary Examiner — Amber D Steele
(74) Attorney, Agent, or Firm — Wolf, Greenfield & Sacks, P.C.

(57) ABSTRACT

In one aspect, the disclosure provides methods of suppressing blood clotting and/or preventing hemorrhage in a subject having extracorporeal membrane oxygenation comprising administering antithrombin. In some embodiments, the antithrombin used in the methods disclosed herein is ATryn®.

14 Claims, No Drawings

(56) References Cited

OTHER PUBLICATIONS

Byrnes, Effect of Antithrombin Supplementation in Pediatric Cardiac Extracorporeal Membrane Oxygenation. American Academy of Pediatrics. National Conference & Exhibition Presentation. New Orleans. Oct. 20-23, 2012.

Niebler et al., Antithrombin replacement during extracorporeal membrane oxygenation. Artif Organs. Nov. 2011;35(11):1024-8.

Sievert et al., Improvement in long-term ECMO by detailed monitoring of anticoagulation: a case report. Perfusion. Jan. 2011;26(1):59-64. doi: 10.1177/0267659110385513. Epub Nov. 5, 2010.

Chang, Transfusion therapy in critically ill children. Pediatr Neonatol. Apr. 2008;49(2):5-12. doi: 10.1016/S1875-9572(08)60004-2.

Ogawa et al., High mortality associated with intracardiac and intrapulmonary thromboses after cardiopulmonary bypass. J Anesth. Feb. 2012;26(1):9-19. doi: 10.1007/s00540-011-1253-x. Epub Oct. 19, 2011.

[No Author Listed] Antithrombin (Recombinant) ATryn for Injection. GTC Biotherapeutics, Inc; US Package Insert: Feb. 3, 2009.

[No Author Listed] GTC Biotherapeutics Expects CHMP to Issue Negative Opinion on ATryn(R). Press Release; Feb. 23, 2006. Last accessed from <http://www.businesswire.com/news/home/20060223005411/en/GTC-Biotherapeutics-Expects-CHMP-Issue-Negative-Opinion> on Nov. 30, 2015.

Bembea et al., Variability in anticoagulation management of patients on extracorporeal membrane oxygenation: an international survey. Pediatr Crit Care Med. Feb. 2013;14(2):e77-84. doi: 10.1097/PCC.0b013e31827127e4.

Berry et al., Comparison of recombinant and plasma-derived antithrombin biodistribution in a rabbit model. Thromb Haemost. Aug. 2009;102(2):302-8. doi: 10.1160/TH09-01-0062.

Byrnes et al., Antithrombin III Supplementation on Extracorporeal Membrane Oxygenation. ASAIO Journal. Jan./Feb. 2014;60(1):57-62.

Edmunds et al., Transgenically produced human antithrombin: structural and functional comparison to human plasma-derived antithrombin. Blood. Jun. 15, 1998;91(12):4561-71.

Levy et al., Recombinant human transgenic antithrombin in cardiac surgery: a dose-finding study. Anesthesiology. May 2002;96(5):1095-102.

Martinez et al., Extracorporeal membrane oxygenation in adults. Contin Edu Anaesth Crit Care Pain. 2012; 12(2):57-61.

Niimi et al., Initial experience with recombinant antithrombin to treat antithrombin deficiency in patients on extracorporeal membrane oxygenation. J Extra Corpor Technol. Mar. 2014;46(1):84-90.

Pal et al., Pharmacology and clinical applications of human recombinant antithrombin. Expert Opin Biol Ther. Jul. 2010;10(7):1155-68. doi: 10.1517/14712598.2010.495713.

Paternoster et al., Efficacy of AT in pre-eclampsia: a case-control prospective trial. Thromb Haemost. Feb. 2004;91(2):283-9.

Warren et al., Caring for the critically ill patient. High-dose antithrombin III in severe sepsis: a randomized controlled trial. JAMA. Oct. 17, 2001; 286(15):1869-78. Erratum in: JAMA Jan. 9, 2002;287(2):192.

Dejongh et al., Recombinant Antithrombin (ATryn) to achieve >80% AT activity in pediatric and neonatal ECMO patients. Poster. Extracorporeal Life Support Organization (ELSO) 26th Annual Conference. Atlanta, Georgia. Sep. 17-20, 2015. One page.

[No Author Listed] Securities and Exchange Commission Form 10-K for the fiscal year ended Dec. 29, 2002. GTC Biotherapeutics, Inc. Filed Mar. 28, 2003. Excerpt.

[No Author Listed] Securities and Exchange Commission Form 10-K for the fiscal year ended Dec. 28, 2003. GTC Biotherapeutics, Inc. Filed Mar. 8, 2004. Excerpt.

[No Author Listed] Securities and Exchange Commission Form 10-K for the fiscal year ended Jan. 2, 2005. GTC Biotherapeutics, Inc. Filed Mar. 15, 2005. Excerpt.

[No Author Listed] Securities and Exchange Commission Form 10-K for the fiscal year ended Jan. 1, 2006. GTC Biotherapeutics, Inc. Filed Mar. 15, 2006. Excerpt.

No Author Listed, FDA clears GTC's ATryn, first US approved drug made from a transgenic animal. The Pharma Letter. 2009. http://www.thepharmletter.com/article/fda-clears-gtc-s-atryn-first-us-approved-drug-mad. Last accessed Dec. 3, 2014. 2 pages.

No Author Listed, Recombinant Human Antithrombin (ATryn) GTC Biotherapeutics. 2007. http://www.wikinvest.com/stock/GTC. Last accessed Dec. 3, 2014. 4 pages.

Bock et al., Cloning and expression of the cDNA for human antithrombin III. Nucleic Acids Res. Dec. 20, 1982;10(24):8113-25.

Briggs et al., Drugs in Pregnancy and Lactation. Ninth Edition. Jan. 7, 2011. Excerpt. Antithrombin III (Human).p. 83-4.

Buck, Control of Coagulation during Extracorporeal Membrane Oxygenation . J Pediatr Pharmacol Ther. Jan. 2005;10(1):26-35. doi: 10.5863/1551-6776-10.1.26.

Chindemi et al., Biodistribution of covalent antithrombin-heparin complexes. Thromb Haemost. Apr. 2006;95(4):629-36.

Cole et al. Glycosylation Patterns of Human Proteins Expressed in Transgenic Goat Milk. Journal of Cellular Biochemistry. 1994, Suppl. 18D, p. 265, Ab. U100, published online Feb. 19, 1994.

Denman et al., Transgenic expression of a variant of human tissue-type Plasminogen activator in goat milk: purification and characterization of the recombinant. Biotechnology, 9:839-843, 1991.

Drohan et al., The Past, Present and Future of Transgenic Bioreactors, Thrombosis and Haemostasis , vol. 78 (1 ): 543-547. 1997.

Ebert et al., Transgenic production of a variant of human tissue-type Plasminogen activator in goat milk: generation of transgenic goats and analysis. Biotechnology, 9:836-838, 1991.

Edmunds et al., Tissue Specific and Species Differences in the Glycosylation Pattern of Antithrombin III, Journal of Cellular Biochemistry, Abstract U102, pp. 265 (1994).

Fan et al., Heterogeneity of recombinant human antithrombin III expressed in baby hamster kidney cells. Effect of glycosylation differences on heparin binding and structure. J Biol Chem. Aug. 15, 1993;268(23):17588-96.

Friedlich, Pharmacokinetic Study of Recombinant AT III in Neonates Undergoing ECMO. Jul. 29, 2013. Last updated Jan. 10, 2015. https://clinicaltrials.gov/ct2/show/NCT01913444. Last accessed Sep. 15, 2016.

Garg, Using reproductive immunology to improve clinical practices. Am J Reprod Immunol. Jun. 2013;69(6):529-32. doi: 10.1111/aji.12119. Epub Apr. 6, 2013.

Houdebine et al., Transgenic animal bioreactors. Transgenic Res. 2000;9(4-5):305-20.

Hughes, 2009 FDA drug approvals. Nat Rev Drug Discov. Feb. 2010;9(2):89-92. doi:10.1038/nrd3101.

Kobayashi et al., Treatment of severe preeclampsia with antithrombin concentrate: results of a prospective feasibility study. Semin Thromb Hemost. Dec. 2003;29(6):645.

Kreuziger et al., Use of recombinant human antithrombin concentrate in pregnancy. Int J Womens Health. Sep. 16, 2013;5:583-6. doi:10.2147/IJWH.S52208. eCollection 2013.

Leiberman et al., Plasma antithrombin III levels in pre-eclampsia and chronic hypertension. Int J Gynaecol Obstet. Aug. 1988;27(1):21-4.

Leitner et al., Recombinant human antithrombin inhibits thrombin formation and interleukin 6 release in human endotoxemia. Clin Pharmacol Ther. Jan. 2006;79(1):23-34.

Maki et al., Antithrombin therapy for severe preeclampsia: results of a double-blind, randomized, placebo-controlled trial. BI51.017 Study Group. Thromb Haemost. Oct. 2000;84(4):583-90.

Menache et al., Evaluation of the Safety, Recovery, Half-Life, and Clinical Efficacy of Antithrombin I11 (Human) in Patients with Hereditary Antithrombin I11 Deficiency. Blood. 1990, vol. 75, pp. 33-39.

Mullins et al., Perspectives Series: Molecular Medicine in Genetically Engineered Animals, Transgenesis in the Rat and Larger Mammals. J. Clin. Invest., vol. 98, No. 11, Suppl., S37-S40. 1996.

Nakabayashi et al., Efficacy of antithrombin replacement therapy in severe early-onset preeclampsia. Semin Thromb Hemost. 1999;25(5):463-6.

(56) References Cited

OTHER PUBLICATIONS

Paidas et al., A Prospective Randomized Evaluation of the Safety and Efficacy of Recombinant Antithrombin in Very Preterm Preeclampsia (PRESERVE-1).Second Clinical Reproductive Immunology Symposium of the American Society for Reproductive Immunology. New Haven, CT. Oct. 27-28, 2012 Poster Presentation.

Paidas et al., Exploring the role of antithrombin replacement for the treatment of preeclampsia: a prospective randomized evaluation of the safety and efficacy of recombinant antithrombin in very preterm preeclampsia (PRESERVE-1). Am J Reprod Immunol. Jun. 2013;69(6):539-44. doi: 10.1111/aji.12091. Epub Feb. 27, 2013.

Sameshima et al., Antithrombin improves fetal condition in women with severe pre-eclampsia before 32 weeks of gestation; a randomized, double-blind, placebo-controlled trial. J Obstet Gynaecol Res. Feb. 2008;34(1):34-9. doi: 10.1111/j.1447-0756.2007.00677.x.

Sibai, Preeclampsia as a cause of preterm and late preterm (near-term) births. Semin Perinatol. Feb. 2006;30(1):16-9.

Tiede et al., Antithrombin alfa in hereditary antithrombin deficient patients: a phase 3 study of prophylactic intravenous administration in high risk situations. Thromb Haemost. Mar. 2008;99(3):616-22. doi:10.1160/TH07-08-0489.

Wall et al., Transgenic Livestock: Progress and Prospects for the Future, Theriogenology 45: 57-68 (1996).

Xu et al., Antithrombin III activity in Chinese women with preeclampsia. Thromb Res. Jul. 15, 1990;59(2):401-6.

\* cited by examiner

USE OF ANTITHROMBIN IN EXTRACORPOREAL MEMBRANE OXYGENATION

RELATED APPLICATIONS

This application is a national stage filing under 35 U.S.C. §371 of international application PCT/US2013/053365, entitled "The Use of Antithrombin in Extracorporeal Membrane Oxygenation," filed Aug. 2, 2013, which was published under PCT Article 21(2) in English, and claims the benefit under 35 U.S.C. §119 of U.S. provisional application 61/679,345 filed Aug. 3, 2012, the entire contents of each of which are incorporated by reference herein in their entireties.

FIELD OF THE INVENTION

The disclosure relates to methods of extracorporeal membrane oxygenation (ECMO).

BACKGROUND OF THE INVENTION

Extracorporeal membrane oxygenation (ECMO) provides cardiac and respiratory support oxygen to patients whose lungs and heart cannot perform this function. ECMO requires careful management of blood flow and anticoagulation. New methods that allow for better regulation of blood flow, prevention of coagulation and improved hemostasis during ECMO are desired.

SUMMARY OF THE INVENTION

In one aspect, the disclosure provides methods of extracorporeal membrane oxygenation. In one embodiment, a method of suppressing blood clotting and/or preventing hemorrhage in a subject having extracorporeal membrane oxygenation, the method comprising administering to a subject having extracorporeal membrane oxygenation a therapeutically effective amount of antithrombin to suppress blood clotting and/or prevent hemorrhage is provided. In one embodiment, the therapeutically effective amount is effective to suppress blood clotting and prevent hemorrhage. In another embodiment, the therapeutically effective amount is also effective to provide anti-inflammatory effects, such as systemic inflammation suppression.

In another embodiment, the antithrombin has a high mannose glycosylation pattern. In another embodiment, the antithrombin has a high fucose glycosylation pattern. In another embodiment, the antithrombin comprises GalNac (N-acetylgalactosamine). In another embodiment, the antithrombin is transgenically produced antithrombin. In another embodiment, the antithrombin is transgenically produced in a goat. In another embodiment, the antithrombin is ATryn®.

In another embodiment, the antithrombin is administered at a dose of 6 units per kg. In another embodiment, the antithrombin is administered at a dose of 80 units per kg. In another embodiment, the antithrombin is administered at a dose of 295 units per kg.

In another embodiment, the antithrombin is administered at a dose sufficient to maintain a level of antithrombin activity present in the blood at the time of initiation of extracorporeal membrane oxygenation.

In another embodiment, the antithrombin is administered in one dose. In another embodiment, the antithrombin is administered by a bolus followed by continuous infusion. In another embodiment, the method further comprises administering heparin.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the Figures. The invention is capable of other embodiments and of being practiced or of being carried out in various ways. Also, the phraseology and terminology used herein is for the purpose of description and should not be regarded as limiting.

DETAILED DESCRIPTION OF THE INVENTION

In one aspect, the disclosure provides methods of suppressing blood clotting and/or preventing hemorrhage in a subject having extracorporeal membrane oxygenation comprising administering to a subject having extracorporeal membrane oxygenation a therapeutically effective amount of antithrombin to suppress blood clotting and/or prevent hemorrhage. In some embodiments, the antithrombin used in the methods disclosed herein is ATryn®.

Extracorporeal Membrane Oxygenation (ECMO)

ECMO is a procedure that provides cardiac and respiratory support oxygen for patients whose heart and lungs cannot perform this function. In an ECMO procedure, cannulae are placed in the patient's blood vessels and the patient's blood is pumped through an ECMO machine. In the ECMO machine, the blood is run over a membrane oxygenator that removes carbon dioxide from the blood and adds oxygen. The blood is taken from the venous system and can be returned to the venous system (veno-venous ECMO) or to the arterial system (veno-arterial ECMO).

ECMO is typically used in patients whose lungs and heart have stopped functioning for a variety of causes, including viral infection (e.g., H1N1 and hRSV) and trauma (e.g., near drowning). ECMO can also be used in newborns with an underdeveloped respiratory system.

The main challenges with ECMO, as in any extracorporeal procedure, are the need to prevent infections and maintain hemostasis to prevent blood clotting (coagulation) and hemorrhage. The prevention of blood clotting and hemorrhage is generally performed by the administration of heparin and/or other anticoagulants. Blood clotting can be monitored by taking blood samples at various time points and measuring the activated clotting time (which should be generally between 140-200 seconds), aPTT (activated partial thromboplastin time), or measurement of anti-Factor Xa levels. Other parameters that can be determined in blood samples to assess hemostasis are the level and the activity of enzymes that act on the coagulation cascade (See e.g., Niebler et al., 2011, Artificial Organs 35: 1024-1028, and Agati et al., 2006, ASAIO Journal 52: 513-516).

Antithrombin and ATryn®

In one aspect, the disclosure provides methods of suppressing blood clotting and/or preventing hemorrhage in a subject having extracorporeal membrane oxygenation comprising administering to a subject having extracorporeal membrane oxygenation a therapeutically effective amount of antithrombin to suppress blood clotting and/or prevent hemorrhage. In some embodiments, the antithrombin has a high mannose glycosylation pattern. In some embodiments, the antithrombin has a high fucose glycosylation pattern. In some embodiments, the antithrombin comprises GalNac (N-acetylgalactosamine). In some embodiments, the antithrombin is transgenically produced antithrombin. In some embodiments, the antithrombin is transgenically produced in a goat. In some embodiments, the antithrombin is ATryn®.

Traditionally, the term "antithrombin" relates to a family of closely related proteins that includes antithrombin I, antithrombin II, antithrombin III and antithrombin IV. However, antithrombin III is the only member of the antithrombin family that has been associated with a significant physiological function, and the current literature often uses the terms antithrombin and antithrombin III interchangeably. Antithrombin, as used herein, refers to antithrombin III, unless specified differently. However, it should be appreciated that members of the antithrombin family other than antithrombin III that have an activity similar to antithrombin III also can be used in the methods disclosed herein.

Generally, antithrombin is a protein of 432 amino acids with a molecular weight of about 58 kDA. However, some non-human antithrombins are 433 amino acids in length. Antithrombin is a serine protease inhibitor that inhibits thrombin and Factor Xa. Antithrombin is naturally found in the serum of mammals including humans. The physiological level of antithrombin in human serum from a healthy individual is about 14-20 mg/dL.

Antithrombin is a glycoprotein that includes four glycosylation sites: Asn96, Asn135, Asn155 and Asn192. Antithrombin occurs both in an alpha form (alpha-antithrombin) and in a beta form (beta-antithrombin), with the alpha form being the most prevalent. The beta form of antithrombin can be distinguished from the alpha form because the beta form is not glycosylated at Asn135. In some embodiments, antithrombin, as used in the methods disclosed herein, includes both the major alpha form of antithrombin and the minor beta form of antithrombin. In some embodiments, antithrombin, as used in the methods disclosed herein, is alpha-antithrombin. In other embodiments, the antithrombin is beta-antithrombin.

Antithrombin is conserved between mammalian species with only minor differences in amino acid sequence. In some embodiments, the species of antithrombin used in the treatment of a subject according to the methods disclosed herein is the same species as the subject. Thus, for instance, human antithrombin (according to its amino acid sequence) is used in methods of treatment in humans, while bovine antithrombin (again according to its amino acid sequence) is used in methods of treatment in bovines. In other embodiments, the species of antithrombin used in the treatment of a subject is from a different species as the subject.

It should further be appreciated that in addition to the amino acid sequence the glycosylation of antithrombin can also be species specific. Thus, for instance, human antithrombin isolated from human plasma (plasma-derived human antithrombin), has a different glycosylation pattern than goat antithrombin isolated from goat plasma. However, as explained below, human antithrombin, for example, may be produced in a goat, providing human antithrombin (antithrombin with a human amino acid sequence) with a glycosylation pattern that mimics the glycosylation of goat antithrombin.

In some embodiments, the antithrombin used in the methods disclosed herein has a high mannose glycosylation pattern. Antithrombin with a high mannose glycosylation pattern, as used herein, refers to an antithrombin in which one or more of the glycosylation side chains comprise an oligomannose or a hybrid type oligosaccharide (in contrast to side chains comprising bi-antennary complex oligosaccharides, which are the predominant side chain structure found in plasma-derived human antithrombin). In some embodiments, the antithrombin used in the methods disclosed herein has a high fucose glycosylation pattern. A high fucose glycosylation pattern, as used herein, refers to antithrombin that has fucose on its proximal GlcNac on a majority of the glycosylation sites that have complex oligosaccharides. In some embodiments, the antithrombin used in the methods disclosed herein comprises GalNac (N-acetylgalactosamine). In some embodiments, the antithrombin used in the methods disclosed herein has a high mannose pattern, a high fucose pattern and includes GalNac. It should be noted that human antithrombin (antithrombin with a human amino acid sequence) that is transgenically produced in goats has a high mannose pattern, a high fucose pattern and includes GalNac, while plasma-derived human antithrombin generally does not have these glycosylation patterns (See e.g., U.S. Pat. No. 5,843,705, U.S. Pat. No. 6,441,145 and U.S. Pat. No. 7,019,193).

The antithrombin used in the methods disclosed herein can be produced through a variety of methods. In some embodiments, the antithrombin is produced by isolation from plasma. In some embodiments, the antithrombin is recombinantly produced. In some embodiments, the antithrombin is transgenically produced.

In some embodiments, the antithrombin used in the methods disclosed herein is transgenically produced. In some embodiments, the transgenically produced antithrombin is produced in a (non-human) mammal. In some embodiments, the transgenically produced antithrombin is produced in an ungulate. In some embodiments, the transgenically produced antithrombin is produced in a goat. It should be appreciated that the antithrombin produced in a first species can be an antithrombin from a second species. Thus, for instance, human antithrombin can be transgenically produced in mice and goats. Similarly, bovine antithrombin can also be transgenically produced in mice and goats. In addition, antithrombin can also be transgenically produced in the species of origin. Thus, goat antithrombin can be transgenically produced in goats.

In some embodiments, the antithrombin used in the methods disclosed herein is transgenically produced. In some embodiments, the transgenically produced antithrombin has a glycosylation pattern that is different from plasma-derived antithrombin. In general, the glycosylation pattern of the antithrombin depends on the species of animal the antithrombin is produced in. Thus, for instance, antithrombin transgenically produced in mice is expected to have a different glycosylation pattern than antithrombin produced in goats.

In some embodiments, the antithrombin used in the methods disclosed herein has the glycosylation pattern of antithrombin transgenically produced in goats.

It should be appreciated that the glycosylation pattern of transgenically produced antithrombin can also depend on the nature of the organ, or body part, of the transgenic animal in which the protein is produced. Thus, the glycosylation pattern of antithrombin produced in the mammary gland is expected to be different from antithrombin produced in the blood, even if produced in the same species. In some embodiments, the antithrombin used in the methods disclosed herein is produced in the mammary gland of a non-human mammal. In some embodiments, the antithrombin used in the methods disclosed herein is produced in the mammary gland of goats.

It should further be appreciated that antithrombin with the glycosylation pattern of antithrombin produced in goats can also be provided by producing or obtaining the antithrombin, for example, in a species other than the goat, and modifying the glycosylation pattern, such as in downstream processing. For instance, glycosylated antithrombin may be produced in mice and the glycosylation pattern of the mice-produced antithrombin may be altered to generate the glycosylation pattern of goat antithrombin by in vitro modification. For instance, the mice-produced antithrombin may be altered through the action of glycosylases or transferases. In addition, the glycosylation pattern may be modified by non-enzymatic (i.e., synthetic) methods.

Antithrombin with the glycosylation pattern of goat produced antithrombin may also be provided by producing antithrombin in cells (e.g., insect cells, bacterial cells) and adding or modifying the glycosylation pattern in downstream processing. Alternatively, antithrombin with the glycosylation pattern of goat produced antithrombin may be provided by isolation from plasma from a non-goat species (or perhaps a different tissue of a goat) and the glycosylation pattern may subsequently be modified in downstream processing.

In some embodiments, the antithrombin used in the methods disclosed herein is ATryn®. ATryn® is a transgenic human alpha-antithrombin that is produced in the goat mammary gland (See e.g., U.S. Pat. No. 5,843,705, U.S. Pat. No. 6,441,145 and U.S. Pat. No. 7,019,193). ATryn® is approved by the FDA for the prevention of peri-operative and peri-partum thromboembolic events in hereditary antithrombin deficient patients. In Europe, ATryn® is approved for use in surgical patients with congenital antithrombin deficiency for the prophylaxis of deep vein thrombosis and thromboembolism in clinical risk situations.

The glycosylation pattern of the goat-produced (human) antithrombin ATryn® differs from the glycosylation pattern of plasma-derived human antithrombin. Because the glycosylation pattern is different, ATryn® has some physiological properties that are different from plasma-derived human antithrombin. For instance, the clearance rate of ATryn® is higher than the clearance rate of plasma-isolated antithrombin (See e.g., U.S. Pat. No. 7,019,193).

Subject

In one aspect, the disclosure provides methods of suppressing blood clotting and/or preventing hemorrhage in a subject having extracorporeal membrane oxygenation comprising administering to a subject having extracorporeal membrane oxygenation a therapeutically effective amount of antithrombin to suppress blood clotting and/or prevent hemorrhage. A "subject", as used herein, is a human or other vertebrate mammal including, but not limited to, mouse, rat, dog, cat, horse, cow, pig, sheep, goat, or non-human primate. In some embodiments, the subject is a human. In some embodiments, the subject is a child.

Heparin and Additional Therapies

In one aspect, the disclosure provides methods of suppressing blood clotting and/or preventing hemorrhage in a subject having extracorporeal membrane oxygenation comprising administering to a subject having extracorporeal membrane oxygenation a therapeutically effective amount of antithrombin to suppress blood clotting and/or prevent hemorrhage. In some embodiments, antithrombin is administered in combination with heparin. Heparin binds antithrombin and increases the protease inhibitor activity of antithrombin. In the embodiments of the disclosure wherein antithrombin is administered in combination with heparin, any combination regimen of administration of antithrombin and heparin is embraced. Thus, in some embodiments, heparin is administered concurrently with antithrombin (e.g. infused at the same time). In some embodiments, heparin is administered prior to, or after, the administration of antithrombin. In some embodiments, the antithrombin and heparin have a partially overlapping administration regimen (e.g., administering only antithrombin for a period of time followed by the administration of a combination of antithrombin and heparin).

In some embodiments of the methods provided herein, no heparin is administered.

In some embodiments, the methods of suppressing blood clotting and/or preventing hemorrhage in a subject having extracorporeal membrane oxygenation comprising administering antithrombin are coupled with additional therapies. In some embodiments, additional therapies are therapies that can be used to suppress blood clotting and/or reduce hemorrhage. These additional therapies include the administration of anticoagulants (in addition to antithrombin or antithrombin together with heparin). Anticoagulants are known in the art and include coumadin, warfarin, acenocoumeral, phenprocoumon, atromentin, brodifacoum, phenindione, fondaparinux, idraparinux, rivaroxaban, apixaban, hirudin, lepirudin, bivalirud, argatroban, dabigatran, ximelegatran, batroxobin and hementin.

In some embodiments, antithrombin (e.g., ATryn®) may also be given with other blood products, such as whole blood, packed red cells, FFP (fresh frozen plasma) or platelets, during ECMO to assist with other deficiencies.

Therapeutically Effective Amount

In one aspect, the disclosure provides methods of suppressing blood clotting and/or preventing hemorrhage in a subject having extracorporeal membrane oxygenation comprising administering antithrombin. In some embodiments, antithrombin is administered in therapeutically effective amounts to suppress blood clotting and/or prevent hemorrhage in extracorporeal membrane oxygenation. The terms "therapeutically effective amount" and "effective amount", which are used interchangeably, refer to the amount necessary or sufficient to realize a desired therapeutic effect(s), e.g., the suppression of blood clotting and/or prevention of hemorrhage. Combined with the teachings provided herein, by choosing among the various active compounds and weighing factors such as potency, relative bioavailability, subject body weight, severity of adverse side-effects and preferred mode of administration, an effective prophylactic or therapeutic treatment regimen can be selected which does not cause substantial toxicity and yet is effective to treat the particular subject.

The effective amount for any particular application can vary depending on such factors as the disease or condition being treated, the particular therapeutic agent(s) to be administered, the size of the subject, or the severity of the disease or disorder. One of ordinary skill in the art can empirically determine the effective amount of antithrombin without necessitating undue experimentation. It is preferred generally that a maximum dose be used, that is, the highest safe dose according to some medical judgment. Multiple doses per day, week or month may be contemplated to achieve appropriate systemic levels of antithrombin. In some embodiments, systemic levels may be achieved by a bolus followed by continuous infusion of antithrombin (e.g., recombinant human antithrombin, ATryn®, etc.) in ECMO. In some embodiments, such administration can provide greater control and precision of anticoagulation than with antithrombin given by intermittent bolus alone. The bolus can be given, for example, intravenously or by intramuscular, intrathecal, or subcutaneous injection. Appropriate systemic levels can be determined by, for example, measurement of the patient's peak or sustained plasma level of antithrombin. Any of the methods of administration can include monitoring of antithrombin levels and/or activity and dose adjustment as needed.

Doses of antithrombin (e.g., ATryn®) to be administered are generally expressed in mg/kg, units of antithrombin per kg, or units of antithrombin per day. In some embodiments, antithrombin is administered at a dose of 1 unit per kg or more, 2 units per kg or more, 5 units per kg day or more, 10 units per kg or more, 20 units per kg or more, 30 units per kg or more, 40 units per kg or more, 50 units per kg or more, 100 units per kg or more, 150 units per kg or more, 200 units per kg or more, 250 units per kg or more, 300 units per kg or more, 350 units per kg or more, 400 units per kg or more, 450 units per kg or more, 500 units per kg or more, 600 units per kg or more, 700 units per kg or more, 800 units per kg or more, 900 units per kg or more, or 1000 units per kg or more. In some embodiments, the antithrombin is administered at a dose of 6 units per kg. In some embodiments, the antithrombin is administered at a dose of 80 units per kg. In some embodiments, the antithrombin is administered at a dose of 295 units per kg.

In some embodiments, antithrombin is administered at a dose of 10 units per day or more, 50 units per day or more, 100 units per day or more, 200 units per day or more, 500 units per day or more, 1000 units per day or more, 1500 units per day or more, 2000 units per day or more, 2500 units per day or more, 3000 units per day or more, 3500 units per day or more, 4000 units per day or more, 4500 units per day or more, 5000 units per day or more, 5500 units per day or more, 6000 units per day or more, 7000 units per day or more, 8000 units per day or more, 9000 units per day or more, 10,000 units per day or more, 15,000 units per day or more, or 20,000 units per day or more.

Doses of antithrombin (e.g., ATryn®) to be administered in the methods disclosed herein can vary depending on the desired therapeutic goal. In some embodiments, the antithrombin is administered at a dose sufficient to maintain a level of antithrombin activity present in the blood at the time of initiation of extracorporeal membrane oxygenation. In some embodiments, the antithrombin is administered at a dose sufficient to exceed the level of antithrombin activity present in the blood at the time of initiation of extracorporeal membrane oxygenation. In some embodiments, the antithrombin is administered at a dose sufficient to obtain at least 50%, at least 60%, at least 70%, at least 80%, at least 90%, at least 100%, at least 110%, at least 120%, at least 130%, at least 140%, at least 200%, at least 300% or more of the antithrombin activity present in the blood at the time of initiation of extracorporeal membrane oxygenation.

In some embodiments, the therapeutically effective amount is administered in one dose. In some embodiments, the therapeutically effective amount is administered in multiple doses. Dosage may be adjusted appropriately to achieve desired levels of antithrombin, local or systemic, depending upon the mode of administration. In the event that the response in a subject is insufficient at such doses, even higher doses (or effective higher doses by a different, more localized delivery route) may be employed to the extent that subject tolerance permits. Multiple doses per day may be contemplated to achieve appropriate systemic levels of compounds.

Administration

In one aspect, the disclosure provides methods of suppressing blood clotting and/or preventing hemorrhage in a subject having extracorporeal membrane oxygenation comprising administering antithrombin. In some embodiments, the antithrombin is administered through continuous infusion. In some embodiments, the antithrombin is administered in one dose.

Antithrombin is typically administered to subjects as pharmaceutical compositions, which may routinely contain pharmaceutically acceptable concentrations of salt, buffering agents, preservatives, compatible carriers, adjuvants, and optionally other therapeutic ingredients. The nature of the pharmaceutical carrier and other components of the pharmaceutical composition will depend on the mode of administration.

The pharmaceutical compositions of the disclosure may be administered by any means and route known to the skilled artisan in carrying out the treatment methods described herein. Preferred routes of administration include, but are not limited to, oral, intravenous, subcutaneous, parenteral, intratumoral, intramuscular, intranasal, intracranial, sublingual, intratracheal, inhalation, ocular, vaginal, and rectal.

Antithrombin, when it is desirable to deliver systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

For oral administration, antithrombin can be formulated readily by combining the compounds with pharmaceutically acceptable carriers well known in the art. Such carriers enable the compounds of the disclosure to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally, the oral formulations may also be formulated in saline or buffers, e.g., EDTA for neutralizing internal acid conditions, or may be administered without any carriers.

For oral delivery, the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Examples of the more common inert ingredients that are used as enteric coatings are cellulose acetate trimellitate (CAT), hydroxypropylmethyl-cellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films. A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic powder; for liquid forms, a soft gelatin shell may be used. The shell material of cachets could be thick starch or other edible paper. For pills, lozenges, molded tablets or tablet triturates, moist massing techniques can be used.

Antithrombin can be included in the formulation as fine multi-particulates in the form of granules or pellets. The formulation of the material for capsule administration could also be as a powder, lightly compressed plugs or even as tablets. The pharmaceutical composition could be prepared by compression. One may dilute or increase the volume of the pharmaceutical composition with an inert material. These diluents could include carbohydrates, especially mannitol, a-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the pharmaceutical composition, such as in a solid dosage form. Materials used as disintegrants include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may also be used. Binders may be used to hold the therapeutic agent together to form a hard tablet and include materials from natural products such as acacia, tragacanth, starch and gelatin. An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Glidants that might improve the flow properties of the drug during formulation and to aid rearrangement during compression might be added. The glidants may include starch, talc, pyrogenic silica and hydrated silicoaluminate.

For administration by inhalation, antithrombin may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas.

Also contemplated herein is pulmonary delivery of antithrombin. Antithrombin may be delivered to the lungs of a mammal for local or systemic delivery. Other reports of inhaled molecules include Adjei et al., 1990, Pharmaceutical Research, 7:565-569; Adjei et al., 1990, International Journal of Pharmaceutics, 63:135-144 (leuprolide acetate); Braquet et al., 1989, Journal of Cardiovascular Pharmacology, 13(suppl. 5):143-146 (endothelin-1); Hubbard et al., 1989, Annals of Internal Medicine, Vol. III, pp. 206-212 (al-antitrypsin); Smith et al., 1989, J. Clin. Invest. 84:1145-1146 (a-l-proteinase); Oswein et al., 1990, "Aerosolization of Proteins", Proceedings of Symposium on Respiratory Drug Delivery II, Keystone, Colo., March, (recombinant human growth hormone); Debs et al., 1988, J. Immunol. 140:3482-3488 (interferon-g and tumor necrosis factor alpha) and Platz et al., U.S. Pat. No. 5,284,656 (granulocyte colony stimulating factor). A method and composition for pulmonary delivery of drugs for systemic effect is described in U.S. Pat. No. 5,451,569, issued Sep. 19, 1995 to Wong et al.

Nasal delivery of a pharmaceutical composition comprising antithrombin is also contemplated. Nasal delivery allows the passage of a pharmaceutical composition to the blood stream directly after administering the composition to the nose, without the necessity for deposition of the product in the lung.

In some embodiments antithrombin is administered locally. Local administration methods are known in the art and will depend on the target area or target organ. Local administration routes include the use of standard topical administration methods such as epicutaneous (application onto the skin), by inhalational, rectal (e.g., by enema or suppository), by eye drops (onto the conjunctiva), ear drops, intranasal route, and vaginal.

Antithrombin may also be formulated in rectal or vaginal compositions such as suppositories or retention enemas, e.g., containing conventional suppository bases such as cocoa butter or other glycerides. In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble analogs, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose analogs, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or one or more auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, 1990, Science 249, 1527-1533, which is incorporated herein by reference.

The agents and compositions described herein may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene- 2-sulphonic, and benzene sulphonic. Also, such salts can be prepared as alkaline metal or alkaline earth salts, such as sodium, potassium or calcium salts of the carboxylic acid group.

The pharmaceutical compositions of the disclosure contain an effective amount of antithrombin included in a pharmaceutically-acceptable carrier. The term pharmaceutically acceptable carrier means one or more compatible solid or liquid filler, diluents or encapsulating substances which are suitable for administration to a human or other vertebrate animal. The term carrier denotes an organic or inorganic ingredient, natural or synthetic, with which the active ingredient is combined to facilitate the application. The components of the pharmaceutical compositions also are capable of being commingled with the compositions of the present disclosure, and with each other, in a manner such that there is no interaction which would substantially impair the desired pharmaceutical efficiency.

Both non-biodegradable and biodegradable polymeric materials can be used in the manufacture of particles for delivering the compositions of the disclosure. Such polymers may be natural or synthetic polymers. The polymer is selected based on the period of time over which release is desired. Bioadhesive polymers of particular interest include bioerodible hydrogels described by Sawhney et al., 1993, Macromolecules 26, 581-587, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

Antithrombin may be contained in controlled release systems. The term "controlled release" is intended to refer to any agents and compositions described herein-containing formulation in which the manner and profile of agents and compositions described herein release from the formulation are controlled. This refers to immediate as well as non-immediate release formulations, with non-immediate release formulations including but not limited to sustained release and delayed release formulations. The term "sustained release" (also referred to as "extended release") is used in its conventional sense to refer to a drug formulation that provides for gradual release of a compound over an extended period of time, and that preferably, although not necessarily, results in substantially constant blood levels of a drug over an extended time period. The term "delayed release" is used in its conventional sense to refer to a drug formulation in which there is a time delay between administration of the formulation and the release of the compound therefrom. "Delayed release" may or may not involve gradual release of a compound over an extended period of time, and thus may or may not be "sustained release." Use of a long-term sustained release implant may be particularly suitable for treatment of chronic conditions. "Long-term" release, as used herein, means that the implant is constructed and arranged to deliver therapeutic levels of the active ingredient for at least 7 days, and preferably 30-60 days. Long-term sustained release implants are well-known to those of ordinary skill in the art and include some of the release systems described above.

Kits

In one aspect, the disclosure provides kits comprising antithrombin (e.g., ATryn®). In some embodiments, the antithrombin is in, or the kit includes, sterile container(s). In some embodiments, the kit comprises a pharmaceutical carrier and instructions for administration of the kit components. In some embodiments, the kit includes a pharmaceutical preparation vial, a pharmaceutical preparation diluent vial, and the antithrombin. The diluent vial may contain a diluent such as physiological saline for diluting what could be a concentrated solution or lyophilized powder of a composition of the disclosure. In some embodiments, the instructions include instructions for mixing a particular amount of the diluent with a particular amount of a concentrated pharmaceutical composition, whereby a final formulation for injection or infusion is prepared. In some embodiments, the instructions include instructions for use in a syringe or other administration device. In some embodiments, the instructions include instructions for treating a patient with an effective amount of a composition of the disclosure. It also will be understood that the containers contained within a kit, with or without containing the preparations, whether the container is a bottle, a vial with a septum, an ampoule with a septum, an infusion bag, and the like, may contain indicia such as conventional markings which change color when the preparation has been autoclaved or otherwise sterilized.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference, in particular for the teaching that is referenced hereinabove. However, the citation of any reference is not intended to be an admission that the reference is prior art.

EXAMPLES

Example 1

ATryn® Administration During Extracorporeal Membrane Oxygenation

Patients are administered ATryn® during ECMO to manage anticoagulation and suppress blood clotting and/or prevent hemorrhage. Heparin is administered at a dose sufficient to maintain a desired activated clotting time (generally between 140-200 seconds). ATryn® is administered as a bolus dose within 24 hours of initiation of ECMO. The dose of ATryn® administered ranges from 2-300 units/kg.

The effect of ATryn® is evaluated by determining the level of antithrombin activity in the blood (See Niebler et al., 2011, Artificial Organs 35: 1024-1028).

Example 2

ATryn® Administration During Extracorporeal Membrane Oxygenation in a Pediatric Population Pediatric patients are administered ATryn® during ECMO to manage anticoagulation and suppress blood clotting and/or prevent hemorrhage. Continuous administration of ATryn® was started at the time of initiation of ECMO. The level of antithrombin activity in the blood is checked and the amount of ATryn® is administered at a dose sufficient to maintain at least 100% antithrombin activity (as compared to the initial level). Heparin is administered at a dose sufficient to maintain a desired activated clotting time of at least 150 seconds (See Agati et al., 2006, ASAIO Journal 52: 513-516)

EQUIVALENTS

The foregoing written specification is considered to be sufficient to enable one skilled in the art to practice the invention. The present invention is not to be limited in scope by examples provided, since the examples are intended as an illustration of certain aspects and embodiments of the invention. Other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

The invention claimed is:

1. A method of suppressing blood clotting and/or preventing hemorrhage in a subject having extracorporeal membrane oxygenation, the method comprising:
    administering to a subject having extracorporeal membrane oxygenation a therapeutically effective amount of recombinant antithrombin to suppress blood clotting and/or prevent hemorrhage.

2. The method of claim 1, wherein the antithrombin has a high mannose glycosylation pattern.

3. The method of claim 1, wherein the antithrombin has a high fucose glycosylation pattern.

4. The method of claim 1, wherein the antithrombin comprises GalNac (N-acetylgalactosamine).

5. The method of claim 1, wherein the antithrombin is transgenically produced antithrombin.

6. The method of claim 5, wherein the antithrombin is transgenically produced in a goat.

7. The method of claim 1, wherein the antithrombin is a transgenic human alpha-antithrombin that is produced in a goat mammary gland.

8. The method of claim 1, wherein the antithrombin is administered at a dose of 6 units per kg.

9. The method of claim 1, wherein the antithrombin is administered at a dose of 80 units per kg.

10. The method of claim 1, wherein the antithrombin is administered at a dose of 295 units per kg.

11. The method of claim 1, wherein the antithrombin is administered at a dose sufficient to maintain a level of antithrombin activity present in the blood at the time of initiation of extracorporeal membrane oxygenation.

12. The method of claim 1, wherein the antithrombin is administered in one dose.

13. The method of claim 1, wherein the antithrombin is administered by a bolus followed by continuous infusion.

14. The method of claim 1, further comprising administering heparin.

* * * * *